United States Patent [19]

Hozumi et al.

[11] 4,408,052
[45] Oct. 4, 1983

[54] PHOSPHOLIPID CARBAMATES

[75] Inventors: Motoo Hozumi, Omiya; Hiroaki Nomura, Takatsuki; Yoshio Yoshioka, Nara, all of Japan

[73] Assignee: Takeda Chemical Industries, Ltd., Osaka, Japan

[21] Appl. No.: 237,970

[22] Filed: Feb. 25, 1981

[30] Foreign Application Priority Data

Feb. 27, 1980 [JP] Japan ................. 55-24333
Oct. 14, 1980 [JP] Japan ................. 55-143980

[51] Int. Cl.³ .................. C07F 9/58; C07F 9/65
[52] U.S. Cl. .................... 546/22; 548/112; 544/157; 544/159; 544/404; 260/938; 260/945; 260/396 R; 424/200
[58] Field of Search .............. 546/22; 424/200; 548/112

[56] References Cited

U.S. PATENT DOCUMENTS 3,681,412 8/1972 Betzing .................. 260/403

FOREIGN PATENT DOCUMENTS 55-2636 1/1980 Japan .................. 260/938
772649 2/1978 South Africa .................. 260/403

*Primary Examiner*—Alan L. Rotman
*Attorney, Agent, or Firm*—Wegner & Bretschneider

[57] ABSTRACT

New carbamic acid esters, inclusive of salts thereof, which have the formula:

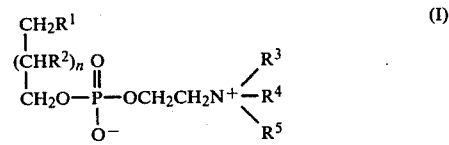

wherein n is zero or 1; $R^1$ and $R^2$ independently represent —H, —OCH$_3$ or —OCONHR$^6$; in which $R^6$ is $C_{8-26}$ aliphatic hydrocarbon residue provided that at least one of $R^1$ and $R^2$ is —OCONHR$^6$; and $R^3$, $R^4$ and $R^5$ independently represent hydrogen or lower alkyl, or

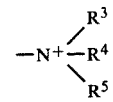

represents cyclic ammonio, exhibit inhibitory activity to multiplication of tumor cells and antimicrobial activity.

5 Claims, No Drawings

PHOSPHOLIPID CARBAMATES

This invention relates to new carbamic acid esters which are of value as pharmaceuticals or antifungal agents.

More particularly, this invention relates to a carbamic acid ester, inclusive of a salt thereof, which has the formula:

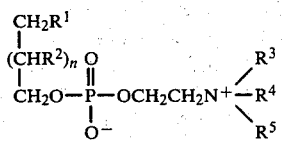 (I)

wherein n is zero or 1; $R^1$ and $R^2$ independently represent —H, —OCH$_3$ or —OCONHR$^6$ in which $R^6$ is $C_{8-26}$ aliphatic hydrocarbon residue provided that at least one of $R^1$ and $R^2$ is —OCONHR$^6$; and $R^3$, $R^4$ and $R^5$ independently represent hydrogen or lower alkyl, or

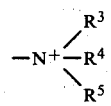

represents cyclic ammonio.

Referring to the above formula (I), the $C_{8-26}$ aliphatic hydrocarbon residue $R^6$ may be a straight-chain or branched group, whether saturated or unsaturated, such as alkyl, alkenyl, alkynyl, etc., which group may optionally be substituted, for example, by OH, mercapto, amino, oxo, carbamoyl, carboxyl, halogen, $C_{3-7}$ cycloalkyl, phenyl, 2,3-dimethoxy-6-methyl-1,4-benzoquinon-5-yl, etc. More specific examples of $R^6$ include $C_{12-22}$ alkyls [e.g. n-octadecyl, n-heptadecyl, pentadecyl, tetradecyl, tridecyl, dodecyl, eicosanyl, docosanyl, dihydrophythyl], $C_{12-22}$ alkenyls [e.g. phythyl, 8-heptadecenyl ($\Delta^8$), 8-tetradecenyl ($\Delta^8$), 8-tridecenyl ($\Delta^8$), 3-tridecenyl ($\Delta^3$), 8,11,14-heptadecatrienyl ($\Delta^{8,11,14}$), 8,11-octadecadienyl ($\Delta^{8,11}$), 4,7,10,13-nonadecatetraenyl ($\Delta^{4,7,10,13}$), 1-heptadecenyl ($\Delta^1$), 12-(2,3-cyclopentenyl)-dodecyl, 12-(2,3-cyclopentenyl)dodecan-5-enyl, 3,7-dimethyl-6-tetradecenyl, 11-hydroxy-8-heptadecenyl, 3,7-dimethyl-9-(2,6,6-trimethyl-1-cyclohexen-1-yl)-2,4,6,8-nonatetraenyl], $C_{16-26}$ aralkyls [e.g. 15-(4-n-butylphenoxy)pentadecyl, ω-p-toluyl-heptadecyl)], 9-(2,3-dimethoxy-5-methyl-1,4-benzoquinon-6-yl)nonanyl, 4,7,10,13-nonadecatetraynyl, tetradecan-8-ynyl, etc.

The lower alkyl groups $R^3$, $R^4$ and $R^5$ may be $C_{1-3}$ alkyls (e.g. methyl, ethyl) and preferably straight-chain alkyls.

The cyclic ammonio group

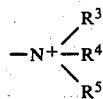

may for example be oxazolio, pyridinio or thiazolio, and may be further substituted by $C_{1-4}$ alkyls (e.g. methyl, ethyl), hydroxyethyl, amino, carbamoyl, ureido, etc. The above cyclic ammonia group may be such that when any two of $R^3$, $R^4$ and $R^5$ form a ring with the quaternary nitrogen atom with the remaining one being, for example, an $C_{1-4}$ alkyl group (e.g. methyl or ethyl), it represents N-methylpiperazinio, N-methylmorpholinio or the like.

In the present compounds, preferred embodiments are compounds (I) wherein n is zero or 1; $R^1$ and $R^2$ independently represent —H, —OCH$_3$ or —OCONHR$^6$ in which $R^6$ is $C_{8-26}$ alkyl, $C_{8-26}$ alkenyl or $C_{8-26}$ alkynyl, each of said groups being unsubstituted or substituted by hydroxyl, mercapto, amino, oxo, carbamoyl, carboxyl, halogen, $C_{3-7}$ cycloalkyl, phenyl or 2,3-dimethoxy-6-methyl-1,4-benzoquinon-5-yl, provided that at least one of $R^1$ and $R^2$ is —OCONHR$^6$; and $R^3$, $R^4$ and $R^5$ independently represent hydrogen or $C_{1-3}$ alkyl, or

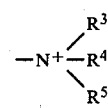

represents oxazolio, pyridinio, thiazolio, N—$C_{1-4}$ alkylpiperazinio or N—$C_{1-4}$ alkylmorpholinio, each of said groups being unsubstituted or substituted by $C_{1-4}$ alkyl, hydroxylethyl, amino, carbamoyl or ureido, or salts thereof.

Particularly preferred species of the various groups in the above formula (I) are: n=1; $R^1$=—OCONHR$^6$ ($R^6$ is $C_{10-18}$ alkyl or alkenyl); $R^2$=—H or —OCH$_3$ and

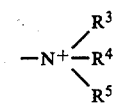

is cyclic ammonio (especially, pyridinio or thiazolio).

The compound of formula (I), wherein n is zero, may be rewriten as:

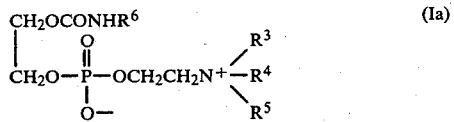 (Ia)

[wherein all the symbols have the meanings defined hereinbefore].

When n is equal to 1, the compound (I) may be represented by the following formulas (Ib), (Ic) and (Id):

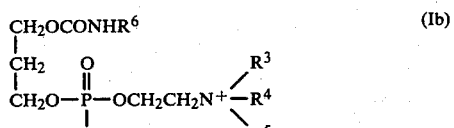 (Ib)

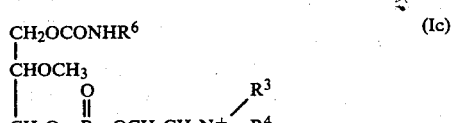 (Ic)

-continued

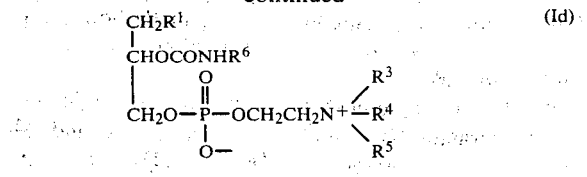

[wherein all the symbols have the meanings defined hereinbefore].

The compound of formula (I) wherein $R^3$, $R^4$ and $R^5$ each is H may also be rewritten as follows.

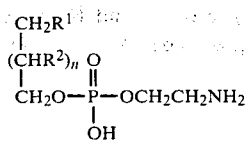

[wherein all the symbols have the meanings defined hereinbefore].

The compound (I) may further exist in the form of a salt such as the one shown below by formula (If) or (Ig).

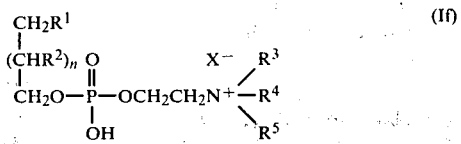

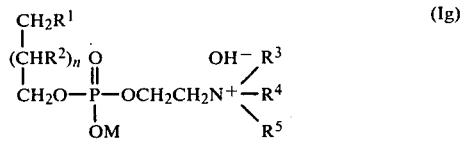

[wherein $X^-$ is anion (e.g. $Cl^-$, $Br^-$ and $I^-$); M is alkali metal (e.g. Na, K) or alkaline earth metal (e.g. Ca); all other symbols have the meanings defined hereinbefore].

As typical examples of the compound (I) according to this invention, there may be mentioned 2-(N-n-dodecylcarbamoyloxy)ethyl 2-trimethylammonioethyl phosphate, 3-(N-n-dodecylcarbamoyloxy)-2-methoxypropyl-2-trimethylammonioethyl phosphate, 3-(N-n-dodecylcarbamoyloxy)propyl 2-aminoethyl phosphate, 3-(N-n-dodecylcarbamoyloxy)propyl 2-trimethylammonioethyl phosphate, 3-(N-n-tridecylcarbamoyloxy)-2-methoxypropyl 2-trimethylammonioethyl phosphate, 3-(N-n-tridecylcarbamoyloxy)propyl 2-trimethylammonioethyl phosphate, 3-(N-n-tridecylcarbamoyloxy)-2-methoxypropyl 2-pyridinioethyl phosphate, 3-(N-n-tridecylcarbamoyloxy-2-methoxypropyl 2-thiazolioethyl phosphate, 3-(N-n-tridecylcarbamoyloxy)propyl 2-pyridinioethyl phosphate, 3-(N-n-tridecylcarbamoyloxy)propyl 2-(4'-carbamoylpyridinio)ethyl phosphate, 3-(N-n-tetradecylcarbamoyloxy)-2-methoxypropyl 2-trimethylammonioethyl phosphate, 3-(N-n-tetradecylcarbamoyloxy)-2-methoxypropyl 2-aminoethyl phosphate, 3-(N-n-tetradecylcarbamoyloxy)-2-methoxypropyl 2-pyridinioethyl phosphate, 3-(N-n-tetradecylcarbamoyloxy)-2-methoxypropyl 2-thiazolioethyl phosphate, 3-(N-n-tetradecylcarbamoyloxy)propyl 2-trimethylammonioethyl phosphate, 3-(N-n-tetradecylcarbamoyloxy)propyl 2-aminoethyl phosphate, 3-(N-n-tetradecylcarbamoyloxy)propyl 2-pyridinioethyl phosphate, 3-(N-n-tetradecylcarbamoyloxy)propyl 2-(4'-aminopyridinio)ethyl phosphate, 3-(N-n-tetradecylcarbamoyloxy)propyl 2-thiazolioethyl phosphate, 3-(N-n-8-heptadecenylcarbamoyloxy)propyl 2-trimethylammonioethyl phosphate, 3-N-n-8,11-heptadecadienylcarbamoyloxy)propyl 2-trimethylammonioethyl phosphate, 3-(N-n-heptadecylcarbamoyloxy)-2-methoxypropyl 2-trimethylammonioethyl phosphate, 3-(N-n-octadecylcarbamoyloxy)-2-methoxypropyl 2-trimethylammonioethyl phosphate, 3-(N-n-octadecylcarbamoyloxy)-2-methoxypropyl 2-pyridinioethyl phosphate, 3-(N-n-octadecylcarbamoyloxy)-2-methoxypropyl 2-thiazolioethyl phosphate.

The compound (I) and its pharmaceutically acceptable salts of this invention have the activity to inhibit multiplication of tumor cells (e.g. mouse leukemia M1, Rauscher virus-induced mouse leukemia, Ehrlich carcinoma, sarcoma 180, B16 melanoma, adenocarcinoma, human myeloid leukemia cell HL-60, clinically isolated primary human cancer cells such as acute myelotic leukemia cells and epithelial malignant tumor cells), and have cell-differentiation-inducing and immunopotentiating activities. Therefore, the present compound produces a remarkable life-extending effect when administered as an antitumor drug to a warm-blooded animal afflicted by malignant tumors such as leukemia or solid cancer (e.g. digestive organ cancer, lung cancer).

The compound (I) is comparatively low-toxic, and causes only remarkably alleviated side effects such as hemolysis, especially when

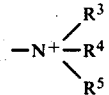

is a cyclic ammonio group such as pyridinio or thiazolio. These side effects are also alleviated when $R^6$ is an alkyl or alkenyl group containing not more than 14 carbon atoms or an alkenyl group containing at least one double bond.

The compound (I) is usually obtained as a crystalline powder or dust and is very much hydrophilic and lipophilic. Therefore, as said antitumor drug, it can be safely administered parenterally or orally as a pharmaceutical composition and in various dosage forms (e.g. injection, tablet, capsule, liquid, ointment). Such an injection, drip infusion or the like can be prepared using physiological saline or an aqueous solution containing glucose and other auxiliary additives. Tablets and capsules can also be prepared in the conventional manner. Such preparations can be administered as unit dosage forms in ways suited to the intended use. Thus, for example, they may be administered intravenously, subcutaneously or otherwise non-orally (e.g. directly to the lesion), or in the case of tablets, capsules, etc., by the oral route. The dosage for tumor-bearing warm-blooded animals generally ranges from about 0.1 to 150 mg/kg body weight or preferably from about 1 to 20 mg/kg body weight, and may be selected within the range according to condition, route of administration and other factors. The administration is usually continuous at the frequency of about 1 to 4 doses daily, although an administration schedule with intervals of 2 to 5 days may be employed in certain cases.

The compound (I) and its pharmaceutically acceptable salts of this invention have a potent antifungal activity against a broad spectrum of fungi. Therefore, the present compound can be used as an antifungal drug (e.g. antimold, antitrichophyton or anticandidal agent) for the treatment and prophylaxis of tinea (athlete's foot) and candidiasis.

Since the compound (I) is only sparingly toxic, it can be orally administered for the above-stated purposes. Usually, however, it is preferable to use it non-orally as a local medication or topical agent. For local administration as an antifungal agent, the compound may be used in finely divided state but it is usually preferable that the compound is used as a pharmaceutical composition in combination with a suitable vehicle or carrier.

The antifungal composition can be prepared in the following and other manners. For example, the compound (I) is dissolved or dispersed in a suitable liquid medium (e.g. solvent) or admixed with a suitable solid carrier (e.g. diluent or volume builder) or adsorbed thereon, with or without addition of suitable additives such as an emulsifier, dispersing agent, suspending agent, extender-adhesive, penetrant, wetting agent, viscosity builder, stabilizer, etc. to prepare such dosage forms as solutions, granules, emulsions, suspensions, ointments, powders, aerosol mists, pastas, cataplasms, etc.

The effective concentration of the antifungal agent (I) in such a preparation cannot be defined in general terms but for the treatment of athlete's foot, for instance, the proportion of (I) is about 0.01 to 70 weight %, preferably about 0.1 to 5 weight % based on the weight of the whole composition. Such an antifungal preparation is applied to the affected body area in the conventional manner, e.g. by means of dressing or spraying over the lesion at the frequency of once to several times daily.

The compound (I) of this invention has potent activity also against a broad spectrum of plant pathogens and especially against fungi. Therefore, it is useful as an agricultural fungicide for the control of plant diseases such as rice blast, rice sheath blight, rice stem rot, cucumber anthracnose and cucumber gray mold.

Such an agricultural fungicide may be used in various forms. Thus, the active compound (I) or its agricultural acceptable salts can be applied directly as a solid bulk product for sustained effects. Alternatively, it may be used as dissolved or dispersed in a suitable liquid medium (e.g. solvent) or admixed with a suitable solid carrier (e.g. diluent or volume builder) or adsorbed thereon, with or without addition of various additives such as an emulsifier, dispersing agent, extender-adhesive, penetrating agent, wetting agent, viscosity builder, stabilizer, etc., in such appropriate dosage forms as oils, emulsifialbe concentrates, wettable powders, solutions, suspensions, dusts, granules, microgranules, tablets, spray mists, etc.

The concentration of (I) in the agricultural fungicide may range from about 10 to 90% in the case of emulsifiable concentrates and wettable powders, about 0.1 to 10% in the case of oils and dusts, and about 5 to 50% in the case of granules. Such emulsifiable concentrates or wettable powders may be diluted (e.g. 50 to 5000-fold) with water or the like. The proportion of active compound (I), the combinations and relative amounts of (I) and other active agents etc. vary with the growth stage and condition of the subject plant, disease, pathological condition, timing and method of application, etc. but it is generally advantageous to apply the fungicide at the rate of about 10 to 300 g of compound (I) per 10 ares.

The application concentration may range from 10 to 1000 ppm of active compound (I). The crop plant may be sprayed, dusted or sprinkled with the fungicide or the seed may be dusted or dipped, and only if the fungicide is safely applied to crops, any application method, use concentration or mode of application can be employed without departing from the scope of this invention.

Since the compound (I) is generally very sparingly active against bacteria and yet has antiprotozoal activity, it can be used advantageously as an antiprotozoal-antifungal agent, for example in the assessment of bacterial ecology in soil, active sludge, animal body fluid or the like. Thus, when useful bacteria are to be isolated from soil samples or when the actions of bacteria are to be evaluated independently of those of protozoa and fungi in connection with the operation and analysis of an active sludge system used in the treatment of waste water, the compound may be utilized to obtain a selective growth of the bacterial flora without permitting growth of the concomitant fungi and protozoa in the specimen. In a typical instance, the sample is added to a liquid or solid medium and 0.1 ml of a 10 $\mu$g/ml to 100 mg/ml solution of the compound (I) is added per ml of the medium, which is then incubated.

The present compound can be produced, for example, by the following methods A, B and C, among others.

Process A

Compound (I) can be obtained by reacting a compound of formula:

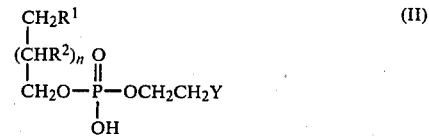

(II)

[wherein Y is Cl, Br or I; other symbols have the meanings defined hereinbefore]
with a compound of formula:

(III)

[wherein symbols have the meanings defined hereinbefore]

Process B

A compound of formula:

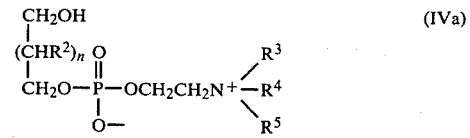

(IVa)

or $$\begin{array}{l}\text{CH}_2\text{R}^1\\|\\\text{CHOH} \quad \text{O} \quad \quad \text{R}^3\\|\quad\quad\parallel\quad\diagup\\\text{CH}_2\text{O}-\text{P}-\text{OCH}_2\text{CH}_2\text{N}^+-\text{R}^4\\\quad\quad\quad|\quad\quad\quad\diagdown\\\quad\quad\quad\text{O}-\quad\quad\quad\text{R}^5\end{array} \quad (\text{IVb})$$

[wherein all symbols have the meanings defined hereinbefore]
is reacted with a compound of formula:

$$R^6-NCO \quad (V)$$

[wherein $R^6$ has the meaning defined hereinbefore]
or reacted with phosgene and, then, with a compound of formula:

$$R^6-NH_2 \quad (VI)$$

[wherein $R^6$ is as defined above]
to obtain the compound (I).

Process C

A compound of formula:

$$\begin{array}{l}\text{CH}_2\text{R}^1\\|\\(\text{CHR}^2)_n \quad \text{O} \quad \text{X}\\|\quad\quad\parallel\diagup\\\text{CH}_2\text{O}-\text{P}\\\quad\quad\quad\diagdown\\\quad\quad\quad\text{X}\end{array} \quad (\text{VII})$$

[X is Cl or Br; other symbols are as previously defined]
is reacted with a compound of formula:

$$\begin{array}{l}\quad\quad\quad\quad\text{R}^3\\\quad\quad\quad\quad\diagup\\\text{HOCH}_2\text{CH}_2\text{N}^+-\text{R}^4.\text{X}^-\\\quad\quad\quad\quad\diagdown\\\quad\quad\quad\quad\text{R}^5\end{array} \quad (\text{VIII})$$

[wherein $X^-$ is an anion, e.g. halogen, $H^-$, $CO_3^{--}$ or sulfate ion; other symbols are as previously defined]
to obtain compound (I).

The compound (III) used in the above Process A, i.e. the formation of quanternary ammonium compound, may for example be trimethylamine, triethylamine, pyridine, thiazole, oxazole, N-methylmorpholine or N-methylpiperazine. This reaction is conducted using an equivalent to large excess (e.g. 50 equiv.) of base (III) per mole of compound (II) at room temperature or under heating (e.g. 35°–200° C.) either in the presence or absence of a solvent. The solvent may for example be methanol, toluene, benzene, ether, dioxane or tetrahydrofuran.

The reaction according to Process B, i.e. the formation of carbamic acid ester, is conducted by reacting 1 to 10 equivalents of (V) with (IVa) or (IVb) in the presence of a solvent such as chloroform, dichloromethane, toluene or pyridine. The reaction temperature is preferably about 0° to 150° C. In the reaction of (IVa) or (IVb) with phosgene, phosgene is reacted at a temperature of about −20° C. to ambient temperature in the presence of a solvent such as toluene, benzene or chloroform, and either as it is or after removal of dissolved phosgene, the reaction mixture is further reacted with (VI) under ice-cooling or at ambient temperature.

Process C is carried out by reacting about 1 to 1.5 equivalents of (VIII) with (VII) in the presence of a solvent (e.g. chloroform, dichloromethane, pyridine, toluene, dioxane) at a temperature between 0° C. and 100° C.

In each of the above-described processes, the progress of reaction can be monitored by thin-layer chromatography and the most suitable reaction conditions can be selected.

The purification of compound obtained by the above reactions can be performed in the conventional manner, e.g. extraction with solvents, recrystallization, chromatography, etc.

When the compound (I) is such that n is 1 and $R^2$ is $-OCH_3$ or $-OCONHR^6$, there may be the D- and L-isomers and a raceme (DL-compound), but all of these forms fall within the scope of compounds (I) according to this invention.

The starting compounds for use in the above processes can be produced for example by the following reaction routes or analogous thereto.

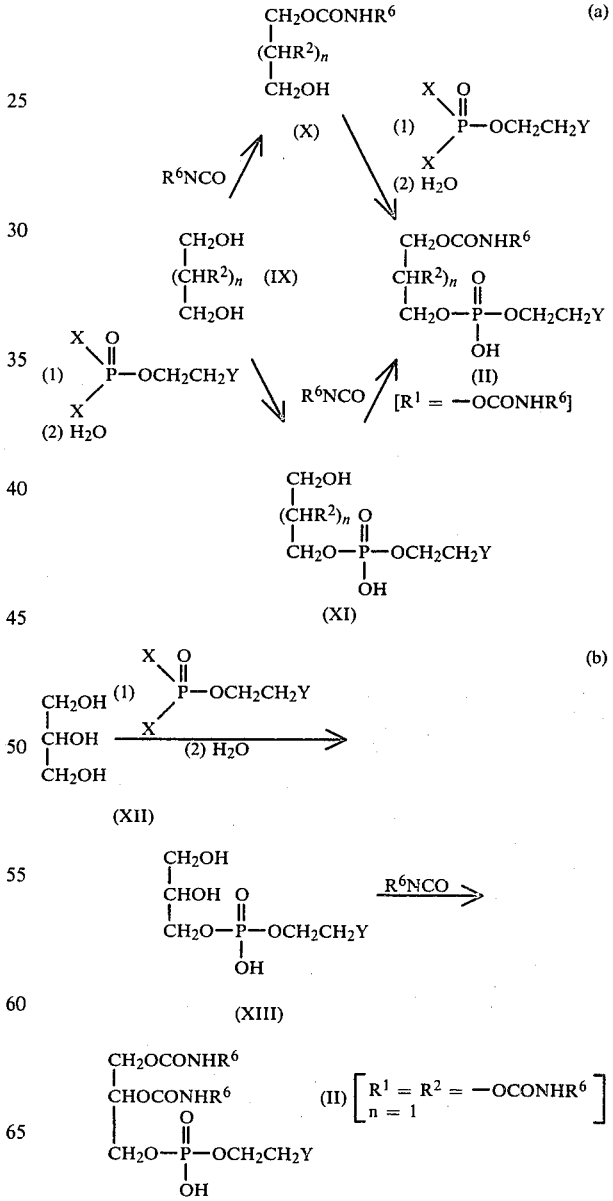

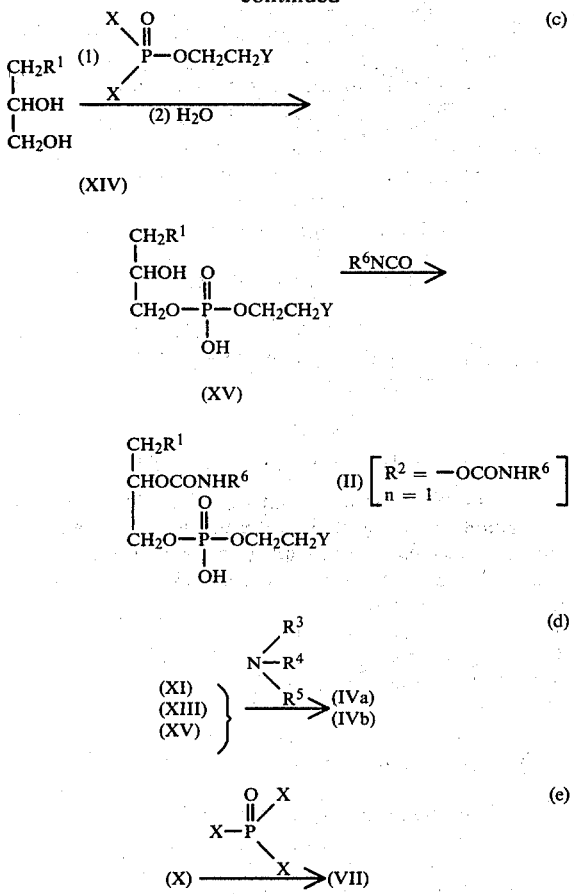

[wherein all symbols have the meanings defined hereinbefore]

The conditions for the above reactions can be selected as in the selection of conditions for Processes A, B and C.

The compound of formula (V) (R⁶—NCO) can be synthesized by reacting the corresponding carboxylic acid with diphenylphosphorylazide [K. Ninomiya, T. Shioiri, S. Yamada: Chem. Pharm. Bull 22, 1398 (1974)], by transforming the carboxylic acid to the corresponding azide which is then thermally decomposed [C. F. H. Allen & A. Bell: Org. Syn., Coll. Vol. 3, 846 (1955)] or by reacting a primary amine $R^1$—$NH_2$ with phosgene [N. W. Farlor: Org. Syn., Coll. Vol. 4, 521 (1963)].

When $R^6$ contains an active substituent group such as $NH_2$, OH or COOH, the group is protected with a protective group which is per se known, the protected compound is then converted to protected (I) via the above-mentioned (V) and process, and finally the protective group is removed by a per se conventional manner.

The following working and test examples are further illustrative but by no means limitative of the invention.

EXAMPLE 1 n-Heptadecyl isocyanate

In 50 ml of toluene is dissolved 5.68 g of stearic acid, followed by addition of 5.5 g of diphenyl phosphorazidate  hereinafter DPPA] and 3.0 ml of triethylamine. The mixture is stirred at room temperature for 2 hours. The reaction mixture is cooled, 100 ml of ether is added and the ether layer is washed with ice-water. The organic layer is taken, dehydrated with a dehydrating agent and refluxed for 2 hours, whereby 5.3 g of the above-indicated compound is obtained as colorless oil.

IR $\nu_{max}^{film}$(cm$^{-1}$): 2920, 2850, 2270 (—NCO), 1680.

EXAMPLE 2

3-(N-n-Heptadecylcarbamoyl)oxypropan-1-ol

In a mixture of 5.7 g of 1,3-propanediol and 30 ml of methylene chloride is dissolved 5.0 g of n-heptadecyl isocyanate and the mixture is stirred at room temperature overnight. To the reaction mixture are added 20 ml each of water and chloroform, and the organic layer is taken and concentrated to dryness. Then, silica gel column chromatography is carried out [eluent:-chloroform-water (97:3)] and the eluate is concentrated to dryness. The procedure provides 3.0 g of the above-indicated compound as colorless crystals.

IR $\nu_{max}^{film}$ (cm$^{-1}$): 3450, 2920, 2850, 1695, 1640, 1530

EXAMPLE 3

3-(N-n-Heptadecylcarbamoyloxy)propyl 2-bromoethyl phosphate

In 14 ml of ethylene chloride-chloroform (5:2) is dissolved 2.5 g of the 3-substituted propanol obtained in Example 2, followed by addition of 1.72 g of bromoethyl phosphrochloridate. The mixture is stirred at room temperature overnight, heated under reflux for 1 hour and cooled. To the reaction mixture is added water (20 ml) and the mixture is warmed for 1 hour. After cooling, extraction is carried out with chloroform, and the chloroform layer is taken and concentrated to dryness. The procedure provides the contemplated product as colorless solid.

EXAMPLE 4

3-(N-n-Heptadecylcarbamoyloxy)propyl 2-trimethylammonioethyl phosphate

The entire amount of the phosphate ester obtained in Example 3 is dissolved in 70 ml of toluene containing 14 g of trimethylamine under anhydrous state and heated at 60° C. for 48 hours. The reaction mixture is concentrated to dryness under reduced pressure, and the residue is dissolved in 40 ml of methanol, vigorously stirred in the presence of 2.7 g of silver carbonate and heated under reflux for 1 hour. After filtration, the filtrate is evaporated to dryness, and the product is separated and purified by silica gel chromatography [eluent: chloroform-methanol-water (65:25:4)] and crystallized from chloroform-acetone. By this procedure is obtained 0.9 g of the above-indicated compound as colorless crystalline powder.

IR $\nu_{max}^{KBr}$(cm$^{-1}$): 1690, 1530, 1460, 1230, 1080, 1050, 950.

NMR(60 MHz, CDCl$_3$): 1.83(2H, —NHCH$_2$—), 3.13(2H, —OCH$_2$CH$_2$CH$_2$O—), 3,40(9H, s, $^+$N(CH$_3$)$_3$), 3.5–4.7(8H, m,

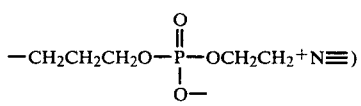

Elemental analysis, for $C_{26}H_{55}N_2O_6P \cdot 0.37H_2O$: Calcd. C, 58.99; H, 10.61; N, 5.29; Found C, 58.99; H, 11.02; N, 5.35

EXAMPLE 5

2,3-Dimethoxy-6-methyl-1,4-benzoquinon-5-yl-n-nonyl isocyanate

In 10 ml of toluene is dissolved 1.4 g of 2,3-dimethoxy-6-methyl-1,4-benzoquinon-5-yl-n-nonanoic acid, and 1.09 g of DPPA and 0.62 ml of triethylamine are added. The mixture is stirred at room temperature for 3 hours. The reaction mixture is promptly extracted with ether and ice-water. The ether layer is taken, dehydrated and concentrated to 5 ml. The product is heated under reflux for 3 hours to give a toluene solution of the contemplated product isocyanate.

EXAMPLE 6

3-[N-(9-(2,3-Dimethoxy-6-methyl-1,4-benzoquinon-5-yl)nonyl)carbamoyloxy]propan-1-ol In pyridine (6 ml) is dissolved 3.0 g (39.5 mM) of 1,3-dihydroxypropane, and the solution is added to the above solution (Example 5). The mixture is stirred at room temperature overnight, concentrated to dryness under reduced pressure and extracted with 20 ml each of water and ether. The ether layer is evaporated to dryness. The product is separated and purified by silica gel chromatography [eluent: $CHCl_3$—MeOH(39:1)]. Light-yellowish brown solid. Yield 1.3 g.

Mass spectrum (m/e): 425(M+), 393(M—$OCH_3$).

IR $\nu_{max}^{film}$(cm$^{-1}$): 1700

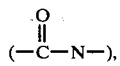

1660, 1650, 1645, 1605(1,4-benzoquinone).

EXAMPLE 7

3-[N-(9-(2,3-Dimethoxy-6-methyl-1,4-benzoquinon-5-yl)-nonyl)carbamoyloxy]propyl 2-bromoethyl phosphate In carbon tetrachloride is dissolved 12 mg of the above 3-hydroxypropyl carbamate, and 45 mg of bromoethyl phosphorodichloridate is added. The mixture is stirred at room temperature for 7 hours. The reaction mixture is evaporated to dryness under reduced pressure, a small amount of water is added and the mixture is stirred in the cold overnight. The mixture is further treated with water and ether, extracted with ether and evaporated to dryness. The residue is purified and isolated by silica gel chromatography to obtain the contemplated product. Yellow solid. Yield 10 mg.

IR $\nu_{max}^{film}$(cm$^{-1}$): 1700, 1665, 1650, 1645, 1610, 1530, 1460, 1450

NMR(60 MHz, $CDCl_3$): 1.0–1.7(16H, m, —($CH_2$)$_8$—), 2.03(3H, s, —$CH_3$), 2.77–3.80(4H, m), 4.03(6H, s, $CH_3O$—)

EXAMPLE 8

3-[N-(9-(2,3-Dimethoxy-6-methyl-1,4-benzoquinon-5-yl)nonyl)carbamoyloxy]propyl 2-trimethylammonioethyl phosphate In 0.5 ml of toluene containing 20% trimethylamine is dissolved 10 mg of the bromide obtained in Example 7 and the mixture is stirred at room temperature for 3 days. The reaction mixture is evaporated to dryness under reduced pressure and the residue is purified by silica gel chromatography [eluent: $CHCl_3$—MeOH—$H_2O$ (60:40:1)]. Red solid. Yield 8 mg.

IR $\nu_{max}^{film}$(cm$^{-1}$): 1700(—CONH—), 1660, 1650, 1640, 1610(1,4-benzoquinone), 1550, 1540(—CONH), 1260, 1230(CN, P-O).

EXAMPLE 9

1-N-n-Octadecylcarbamoyl-2-methylglycerol

In 20 ml of pyridine are stirred 9.7 g of n-octadecyl isocyanate and 3.5 g of β-methylglycerolether and the mixture is further stirred at room temperature overnight. The reaction mixture is poured into a mixture of 300 ml of ether and 50 ml of water and the whole mixture is neutralized with concentrated hydrochloric acid. The ether layer is separated, washed with water, dried, and concentrated to dryness. The residue is purified by silica gel chromatography [eluent: chloroform-ether (1:1)] to yield 8.2 g of colorless crystals.

IR $\nu_{max}^{Nujol}$(cm$^{-1}$): 3340, 1687.

mp 55°–56° C.

Mass spectrum (m/e): 401(M+), 370(M—$OCH_3$)

EXAMPLE 10

3-(N-n-Octadecylcarbamoyloxy)-2-methoxypropyl 2-bromoethyl phosphate

In 30 ml of carbon tetrachloride is dissolved 6.0 g of glycerol obtained in Example 9, followed by addition of 4.0 g of bromoethyl phosphorodichloridate. The mixture is heated under reflux for 18 hours. After cooling, the solvent is distilled off, and 50 ml of water is added to the reaction mixture and heated under reflux for 1 hour. After cooling, extraction is carried out with ether. The ether layer is separated, washed with water, dried and concentrated to dryness. The procedure provides the contemplated product as colorless solid.

IR $\nu_{max}^{Nujol}$(cm$^{-1}$): 3320, 1690.

EXAMPLE 11

3-(N-n-Octadecylcarbamoyloxy)-2-methoxypropyl 2-trimethylammonioethyl phosphate

In 60 ml of toluene containing 10 g of trimethylamine is dissolved 2.0 g of the phosphate ester obtained in Example 10, and the solution is allowed to stand at room temperature for 3 days. The reaction mixture is concentrated to dryness under reduced pressure, the residue is dissolved in 50 ml of methanol, and 2 g of silver carbonate is added. The mixture is refluxed for 1 hour and, then, filtered. The filtrate is evaporated to dryness, and the residue is separated and purified by silica gel chromatography [eluent: chloroform-methanol-water (65:25:4)] and crystallized from chloroform-acetone. By this procedure is obtained 640 mg of the contemplated product as colorless powders.

IR $\nu_{max}^{KBr}$(cm$^{-1}$): 3350, 1700, 1542, 1470, 1250, 1090, 1060.

NMR(60 MHz, CDCl₃): 0.7–1.8(35H), 2.9–4.6(11H, m), 3.46(9H, s, Me₃N), 3.50(3H, s, OCH₃).

Elemental analysis, for $C_{28}H_{59}N_2O_7P \cdot 1.5H_2O$: Calcd. C, 56.63; H, 10.52; N, 4.72; P, 5.22; Found C, 56.37; H, 10.70; N, 4.91; P, 5.38

EXAMPLE 12

3-(N-n-Octadecylcarbamoyloxy)-2-methoxypropyl 2-pyridinioethyl phosphate

In 20 ml of pyridine is dissolved 2.0 g of the phosphate ester obtained in Example 11, and the solution is warmed at 60° C. overnight. The pyridine is distilled off under reduced pressure and 50 ml of methanol and 2 g of silver carbonate are added to the residue. The mixture is heated under reflux for 2 hours. After filtration, the filtrate is evaporated to dryness, and the product is separated and purified by silica gel chromatography [eluent: chloroform-methanol-water (65:25:4)] and crystallized from chloroform-acetone to obtain the contemplated product.

IR $\nu_{max}^{KBr}$(cm⁻¹): 3340, 1698, 1540, 1470, 1255, 1075, 1050.

NMR(60 MHz, CDCl₃): 0.7–1.8(35H), 3.44(3H, s, OCH₃), 2.9–4.8(9H, m), 5.20(2H, broad CH₂N⁺≡), 6.16(1H, broad, CONH), 8.0–8.8(3H, m, pyridinio), 9.58(2H, m, pyridinio).

Elemental analysis, for $C_{30}H_{55}N_2PO_7 \cdot H_2O$: Calcd. C, 59.58; H, 9.50; N, 4.63; P, 5.12; Found C, 59.95; H, 9.60; N, 4.61; P, 5.30

EXAMPLE 13

3-(N-n-Octadecylcarbamoyloxy)-2-methoxypropyl 2-thiazolioethyl phosphate

A mixture of 2.0 g of the phosphate ester obtained in Example 10 and 4.5 g of thiazole is stirred and warmed at 60° C. for 5 days. The thiazole is distilled off under reduced pressure, and 50 ml of methanol and 2 g of silver carbonate are added to the residue. The mixture is heated under reflux for 2 hours. After filtration, the filtrate is evaporated to dryness, and the residue is separated and purified by silica gel chromatography [eluent: chloroform-methanol-water (65:25:4)] and crystallized from chloroform-acetone to obtain the contemplated product.

IR $\nu_{max}^{KBr}$(cm⁻¹): 3400, 2920, 2851, 1701, 1558, 1246, 1065.

NMR(60 MHz, CDCl₃): 0.7–1.8(35H), 3.46(3H, s, OCH₃), 2.9–4.8(9H, m), 5.08(2H, broad, CH₂N⁺≡), 6.30(1H, broad, CONH), 8.55(1H, broad, thiazolio), 8.88(1H, broad, thiazolio), 10.97(1H, broad, thiazolio).

Elemental analysis, for $C_{28}H_{53}N_2O_7PS \cdot 1.5H_2O$: Calcd. C, 54.26; H, 9.11; N, 4.52; P, 5.00 Found C, 54.30; H, 8.90; N, 4.71; P, 5.03

EXAMPLE 14

2-(N-Octadecylcarbamoyloxy)ethanol

In 50 ml of pyridine are dissolved 11.8 g (40 mM) of stearyl isocyanate and 12.4 g (200 mM) of ethylene glycol, and the solution is allowed to stand at room temperature overnight. The reaction mixture is concentrated to dryness under reduced pressure, and the residue is recrystallized from 100 ml of methanol to give 11.38 g (yield 79.5%) of the contemplated product. mp. 81°–82° C.

EXAMPLE 15

2-(N-Octadecylcarbamoyloxy)ethyl 2-trimethylammonioethyl phosphate

In 12 ml of chloroform is dissolved 4.0 g of 2-(N-stearylcarbamoyloxy)ethanol (11.24 mM) followed by addition of 2.72 g (11.24 mM) of 2-bromoethyl phosphorodichloridate. The mixture is heated under reflux for 2 hours, followed by addition of 40 ml of water. The mixture is further refluxed for 3 hours, further followed by addition of 40 ml of chloroform. The chloroform layer is taken and concentrated to dryness under reduced pressure, the residue is dissolved in 20% trimethylamine-toluene solution, and the solution is heated in a sealed tube at 60° C. for 2 days. The reaction mixture is concentrated to dryness under reduced pressure, and the residue is dehalogenated with silver carbonate in methanol, adsorbed on silica gel (40 g) and eluted with chloroform-methanol-water (65:25:4). The desired product fractions are pooled and concentrated to dryness under reduced pressure. The residue is dissolved in a small amount of chloroform, followed by gradual addition of acetone. The procedure provides 4.1 g (69.9%) of the contemplated compound as colorless powders.

IR(KBr): 3420, 2910, 2850, 1700, 1540, 1465, 1240, 1080, 1050, 965 (cm⁻¹)

Elemental analysis, for $C_{26}H_{55}N_2O_6P \cdot H_2O$: Calcd. C, 57.75; H, 10.62; N, 5.18; P, 5.73; Found C, 57.72; H, 10.64; N, 5.28; P, 5.89

EXAMPLE 16

3-(N-8,11,14-Heptadecatrienylcarbamoyloxy)propanol

In 50 ml of toluene is dissolved 5.56 g (20 mM) of linolenic acid, followed by addition of 5.5 g (20 mM) of diphenyl phosphoroazidate and 3.0 ml of triethylamine. The mixture is stirred for 2 hours, concentrated to about 25 ml and heated under reflux for 3 hours. Then, 50 ml of pyridine containing 6.0 g. (78.9 mM) of propandiol is added to the residue, and the mixture is stirred overnight. The reaction mixture is concentrated to dryness under reduced pressure, and the residue is adsorbed on silica gel (50 g) and eluted with 2% methanol-chloroform. The procedure provides 4.0 g (yield 68.4%) of the contemplated compound.

IR(film): 3350, 3010, 2960, 2930, 2860, 1700, 1540, 1465, 1270, 1140, 1060 (cm⁻¹)

EXAMPLE 17

3-(N-8,11,14-Heptadecatrienylcarbamoyloxy)propyl 2-trimethylammonioethyl phosphate In 20 ml of chloroform is dissolved 4.0 g (11.396 mM) of 3-(N-8,11,14-heptadecatrienylcarbamoyloxy)-propanol, followed by addition of 1.74 g (11.396 mM) of 2-bromoethyl phosphorodichloridate. The mixture is heated under reflux for 2 hours. After cooling, 20 ml each of water and chloroform are added to the residue. The mixture is vigorously stirred, and the chloroform layer is taken and concentrated to dryness under reduced pressure. The residue is dissolved in 60 ml of 2% trimethylamine-toluene solution, and the solution is heated in a sealed tube at 60° C. for 2 days. The reaction mixture is concentrated to dryness under reduced pressure, and the residue (the HBr salt of contemplated compound) is dehalogenated with methanol and silver carbonate, adsorbed on a silica gel column (40 g) and eluted with an eluent [chloroform-methanol-water (65:25:4)]. The desired product fractions are pooled and concentrated to dryness. The residue is washed with n-hexane to give 3.2 g (yield 50.9%) of the contemplated compound as syrup.

IR(film): 3350, 3010, 2970, 2935, 2855, 1700, 1540, 1480, 1230, 1140, 1085, 1055, 970 (cm$^{-1}$)

Elemental analysis, for $C_{26}H_{49}N_2O_6P \cdot 2H_2O$: Calcd. C, 56.50; H, 9.67; N, 5.07; P, 5.60; Found C, 56.40; H, 9.54; N, 5.47; P, 5.98

EXAMPLE 18

3-[8,11,14(Z,Z,Z)-Heptadecatrienylcarbamoyloxy]-propanol

In 50 ml of toluene are dissolved 5.56 g (20 mM) of linolenic acid and 6.0 g (22 mM) of diphenyl phosphoroazidate, followed by gradual addition of 3.3 ml of triethylamine. The mixture is stirred at room temperature for 2 hours, concentrated to about 25 ml and heated under reflux for 2 hours. The residue is poured into 50 ml of pyridine containing 6.0 g of 1,3-propanediol, and the mixture is stirred at room temperature overnight. The reaction mixture is concentrated to dryness under reduced pressure, and 50 ml each of water and ethyl acetate are added to the residue. The mixture is vigorously stirred, and the ethyl acetate layer is taken, concentrated to dryness under reduced pressure and adsorbed on a silica gel column (50 g). Elution is carried out with chloroform and the fractions giving an $R_f$ value of 0.50 (TLC, silica gel, CHCl$_3$) are pooled. Yield 4.0 g.

IR(film)cm$^{-1}$: 3330, 3000, 2960, 2930, 2850, 1700, 1540, 1460, 1260, 1140, 1055.

EXAMPLE 19

3-[8,11,14(Z,Z,Z)-Heptadecatrienylcarbamoyloxy]-propyl 2-aminoethyl phosphate

In 30 ml of benzene is dissolved 4.24 g (12.04 mM) of 3-[8,11,14(Z,Z,Z)-heptadecatrienylcarbamoyloxy]-propanol (1), and 4.82 g (15.65 mM) of 2-(phthalimido)ethyl phosphorodichloridate and 1.24 g (15.65 mM) of pyridine are added dropwise to the mixture. The whole mixture is stirred at room temperature for 2 hours and concentrated to dryness under reduced pressure. The residue is hydrolyzed with 70% pyridine-water and reconcentrated to dryness under reduced pressure. Then, 10% HCl is added to the residue and extraction is carried out with ether. The extract is dissolved in a methanol solution containing 3.0 g of hydrazine hydrate and the solution is heated under reflux for 30 minutes. The precipitated insolubles are filtered off when hot and the mother fluid is concentrated to dryness under reduced pressure. The residue is purified by silica gel chromatography and lastly reprecipitated from chloroform-acetone to obtain the contemplated compound as colorless powders. Thin layer chromatography [silica gel: CHCl$_3$—MeOH—H$_2$O (65:25:4)] $R_f$=0.26

IR(KBr)cm$^{-1}$: 3350, 3005, 2930, 2850, 1690, 1540, 1260, 1240, 1210, 1140, 1080, 1000, 915, 830, 730.

Elemental analysis for $C_{23}H_{43}NO_6P \cdot H_2O$: Calcd. C, 56.08; H, 9.21; N, 5.69; P, 6.29; Found C, 56.08; H, 9.01; N, 5.79; P, 6.07

EXAMPLE 20

3-[8,11(Z,Z)-Heptadienylcarbamoyloxy]propyl 2-trimethylammonioethyl phosphate

In 6.5 ml of chloroform is dissolved 1.8 g (5.3 mM) of 3-[8,11(Z,Z)-heptadienylcarbamoyloxy]propnaol (synthesized as in Example 18), followed by addition of 1.28 g (5.3 mM) of 2-bromoethyl phosphorodichloridate. The mixture is heated under reflux for 3 hours, and the reaction mixture is concentrated to dryness under reduced pressure. Then, 20 ml of water is added to the residue, and the mixture is heated under reflux. Extraction is carried out with 20 ml of chloroform, and the chloroform layer is concentrated to dryness under reduced pressure. The residue is dissolved in 50 ml of 20% trimethylamine-toluene, and the solution is heated in a sealed tube at 65° C. for 48 hours. The reaction mixture is concentrated to dryness under reduced pressure. The residue is dissolved in 25 ml of methanol, followed by addition of 1.8 g of Ag$_2$CO$_3$. The mixture is heated under reflux and filtration is carried out when hot. The filtrate is concentrated to dryness under reduced pressure. The residue is purified by silica gel chromatography to obtain 0.5 g of the contemplated compound as colorless solid.

IR(film)cm$^{-1}$: 3500, 3010, 2960, 2940, 2860, 1700, 1540, 1460, 1230, 1140, 1090, 1060, 970.

Elemental analysis for $C_{26}H_{51}N_2O_6P \cdot 2H_2O$: Calcd. C, 56.29; H, 9.79; N, 5.05; P, 5.58; Found C, 56.22; H, 9.63; N, 5.18; P, 5.48

EXAMPLE 21

2-[8,11(Z,Z)-Heptadecadienylcarbamoyloxy]ethyl 2-trimethylammonioethyl phosphate In chloroform is dissolved 1.8 g (5.69 mM) of 2-[8,11(Z,Z)-heptadecadienylcarbamoyloxy]ethanol (synthesized as in Example 18), followed by addition of 1.38 g (5.69 mM) of 2-bromoethyl phosphorodichloridate. The mixture is heated under reflux for 3 hours and purified as in Example 20 to obtain the contemplated compound as colorless solid. 250 mg.

IR(film)cm$^{-1}$: 3450, 3000, 2950, 2920, 1700, 1540, 1460, 1225, 1080, 1050, 960.

Elemental analysis for $C_{25}H_{49}N_2O_6P \cdot 2H_2O$: Calcd. C, 55.54; H, 9.88; N, 5.18; P, 5.73; Found C, 55.53; H, 9.97; N, 5.29; P, 5.59

EXAMPLE 22

3-[8,11(Z,Z)-Heptadecadienylcarbamoyloxy]propyl 2-aminoethyl phosphate

In benzene are dissolved 2.8 g (8.3 mM) of 3-[8.11-(Z,Z)-heptadecadienylcarbamoyloxy]propanol and 3.32 g of 2-(phthalimido)ethyl phosphorodichloridate, followed by addition of 0.85 g (10.8 mM) of pyridine. The mixture is stirred at room temperature for 2 hours. Then, as in Example 19, the reaction mixture is hydrolyzed, dephthaloylated and purified by silica gel chromatography to obtain 2.1 g of the contemplated compound as colorless powder.

IR(film)cm$^{-1}$: 3350, 3000, 2960, 2920, 2850, 1690, 1630, 1540, 1460, 1240, 1210, 1140, 1080, 1000, 920.

Elemental analysis for $C_{23}H_{45}N_2O_6P \cdot 2H_2O$: Calcd. C, 57.54; H, 9.60; N, 5.96; P, 6.45; Found C, 57.53; H, 9.53; N, 5.83; P, 6.49

EXAMPLE 23

3-(N-Tridecylcarbamoyloxy)propyl 2-trimethylammonioethyl phosphate

In 23 ml of benzene are dissolved 4.0 g (13.27 mM) of 3-(N-tridecylcarbamoyloxy)propanol prepared from 9.12 g of myristic acid as in Example 18 and 4.82 g (19.90 mM) of 2-bromoethyl phosphorodichloridate. To the solution is added dropwise 1.57 g (19.90 mM) of pyridine, and the mixture is stirred at room temperature. As in Example 20, the reaction mixture is hydrolyzed, converted to a quaternary ammonium compound, dehalogenated and purified by silica gel chromatography to give the contemplated compound as colorless solid. Yield 3.5 g.

IR(film)cm$^{-1}$: 2830, 2930, 2850, 1700, 1530, 1460, 1240, 1120, 1080, 1055, 965, 920, 830, 760.

Elemental analysis for $C_{22}H_{47}N_2O_6P.O.6H_2O$: Calcd. C, 55.35; H, 10.18; N, 5.87; P, 6.49; Found C, 55.32; H, 10.34; N, 5.81; P, 6.51

EXAMPLE 24

3-N-Tetradecylcarbamoyl-2-methylglycerol

In 200 ml of dry toluene is dissolved 20 g of pentadecanoic acid, followed by addition of 27.3 g of diphenyl phosphoroazidate and 14.9 ml of triethylamine. The mixture is stirred at room temperature for 5 hours. After the reaction mixture is concentrated under reduced pressure, the concentrate is heated under reflux for an hour. After cooling, 32.8 g of β-methylglycerol and 124 ml of dry pyridine are added to the reaction mixture. The mixture is stirred at room temperature overnight. Then, the reaction mixture is concentrated to dryness and the residue is dissolved in chloroform, washed with water, dried and purified by silica gel chromatography (eluent: chloroform) to obtain 9.43 g (33%) of the contemplated compound.

IR $\nu_{max}^{KBr}$(cm$^{-1}$): 1695

EXAMPLE 25

3-N-(Tetradecylcarbamoyloxy)-2-methoxypropyl 2-aminoethyl phosphate

In 30 ml of benzene is dissolved 4 g of the glycerol obtained in Example 24, followed by addition of 5.4 g of 2-(phthalimido)ethyl phosphorodichloridate and 1.6 g of dry pyridine. The mixture is stirred at room temperature for about 4 hours, at the end of which time it is concentrated to dryness. To the residue is added 19 ml of 70% aqueous pyridine solution and the mixture is stirred at 70° C. for 1.3 hours. After cooling, the reaction mixture is made acidic with hydrochloric acid and extracted with ether. The extract is washed with water, dried and concentrated. The residue is dissolved in methanol, 1.7 g of hydrazine hydrate added and the mixture stirred at room temperature for 30 minutes. The reaction mixture is concentrated to dryness, purified by silica gel chromatography and recrystallized from methanol to give 2.47 g (46%) of white powder.

IR$\nu_{max}^{KBr}$cm$^{-1}$: 3325, 2920, 2851, 1689, 1550, 1460, 1240, 1215, 1079.

mp: 185°-190° C.

Elemental analysis for $C_{21}H_{45}N_2O_7P$: Calcd. C, 53.83; H, 9.68; N, 5.98; P, 6.61; Found C, 53.61; H, 9.59; N, 5.95; P, 6.68

EXAMPLE 26

3-(N-Tetradecylcarbamoyloxy)-2-methoxypropyl 2-trimethylammonioethyl phosphate In 25 ml of benzene is dissolved 5.4 g of the glycerol obtained in Example 24, followed by addition of 4.9 g of bromoethyl phosphorodichloridate and 1.6 g of pyridine. The mixture is stirred at room temperature for 3 hours, at the end of which time it is concentrated to dryness. To the residue is added water and the mixture is heated under reflux. After cooling, the reaction mixture is made acidic with hydrochloric acid and extracted with chloroform. The extract is washed with water, dried and concentrated to dryness. The residue is dissolved in toluene containing 10 g of trimethylamine and the mixture is warmed at 60° C. for 48 hours. The reaction mixture is concentrated to dryness, the residue is dissolved in methanol, and 6 g of silver carbonate is added to the solution. The mixture is heated under reflux for a while and filtration is carried out when hot. The filtrate is concentrated to dryness, purified by silica gel chromatography and recrystallized from a chloroform-acetone mixture to give 2.0 g (25%) of the contemplated compound.

IR(film): 3325, 2920, 2850, 1699, 1530, 1460, 1228, 1080 (cm$^{-1}$)

Elemental analysis for $C_{24}H_{51}N_2O_7P.H_2O$: Calcd. C, 54.52; H, 10.11; N, 5.30; P, 5.86; Found C, 54.48; H, 10.06; N, 5.15; P, 5.88

EXAMPLE 27

3-N-Decylcarbamoyl-2-methylglycerol

In 220 ml of toluene is dissolved 25 g of n-undecanoic acid, followed by addition of 51.6 g of diphenyl phosphoroazidate and 28.3 ml of triethylamine. The mixture is stirred at room temperature for 3.5 hours. The reaction mixture is concentrated to 70 ml and heated under reflux for 1.5 hours. After cooling, 53.3 g of β-methylglycerolether and 155 ml of pyridine are added. The mixture is stirred at room temperature overnight and concentrated to dryness. The residue is dissolved in chloroform, washed with water, dried and concentrated. Then, silica gel chromatography is carried out to give 20.7 g (53%) of the contemplated compound.

IR(film): 3340, 2920, 2850, 1700, 1255, 1065, 955, 748 (cm$^{-1}$)

EXAMPLE 28

3-(N-Decylcarbamoyloxy)-2-methoxypropyl 2-aminoethyl phosphate

In 45 ml of benzene is dissolved 5 g of the glycerol obtained in Example 27, followed by addition of 7.5 g of 2-(phthalimido)ethylphosphorodichloridate and 2.05 g of pyridine. The mixture is stirred at room temperature for 3 hours, and the solvent is distilled off. To the residue is added 27 ml of 70% aqueous pyridine solution and the mixture is stirred at 70° C. for 1.5 hours. After cooling, extraction is carried out with ether. Then, as in Example 25, hydrazinolysis and after-treatment are carried out. The product is purified by silica gel chromatography and further recrystallized from ethanol to give 2.6 g (37%) of white powder.

IR $\nu_{max}^{KBr}$(cm$^{-1}$): 3324, 2925, 2851, 1689, 1550, 1460, 1240, 1215, 1080.

Elemental analysis for $C_{17}H_{37}N_2O_7P$: Calcd. C, 49.48; H, 8.66; N, 6.86; P, 7.61; Found C, 49.50; H, 9.04; N, 6.79; P, 7.51

EXAMPLE 29

3-(N-Decylcarbamoyloxy)-2-methoxypropyl 2-trimethylammonioethyl phosphate

In benzene are dissolved 7 g of the glycerol obtained in Example 27 and 7.6 g of bromoethyl phosphorodichloridate, and 2.5 g of pyridine is added dropwise to the solution. The mixture is stirred at room temperature for 3 hours. The reaction mixture is concentrated, 50 ml of water is added to the residue and the mixture is heated under reflux. After cooling, extraction is carried out with ether. The extract is washed with water and dried, the solvent is distilled off and a toluene solution containing 14 g of trimethylamine is added thereto. The mixture is warmed at 60° C. Then, the reaction mixture is concentrated to dryness, dissolved in methanol and dehalogenated with 9.3 g of silver carbonate. The product is purified by silica gel chromatography and recrystallized from chloroform-acetone to give 1.0 g (9%) of the contemplated compound.

Elemental analysis for $C_{24}H_{51}N_2O_7P.H_2O$: Calcd. C, 54.48; H, 10.06; N, 5.15; P, 5.88; Found C, 54.52; H, 10.11, N, 5.30; P, 5.86

IR $\nu_{max}^{KBr}$ (cm$^{-1}$): 2920, 1695, 1230, 1080

EXAMPLE 30

3-N-Dodecylcarbamoyloxypropanol

In 50 ml of toluene is dissolved 4.26 g of tridecanoic acid, followed by addition of 6.05 g diphenyl phosphoroazidate and 3.1 ml of triethylamine. The mixture is stirred at room temperature for 2 hours. The reaction mixture is concentrated to 20 ml and heated under reflux for 1 hour. After cooling, 50 ml of pyridine containing 4.56 g of trimethylene glycol is added and the mixture is stirred overnight. The solvent is distilled off and the residue is dissolved in chloroform, washed with water and dried. The product is subjected to silica gel chromatography to give 3.88 g (79.5%) of the contemplated compound.

IR $\nu_{max}^{KBr}$ (cm$^{-1}$): 1685

EXAMPLE 31

3-N-Dodecylcarbamoyloxypropyl 2-trimethylammonioethyl phosphate

In benzene are dissolved 2.86 g of the 3-hydroxypropyl carbamate obtained in Example 30 and 3.63 g of bromoethyl phosphorodichloridate, and 1.19 g of pyridine is added dropwise. The mixture is stirred at room temperature and the solvent is distilled off. Water is added to the residue and the mixture is refluxed for a while. After cooling, extraction is carried out with ether and the ether is distilled off. The residue is dissolved in 25 ml of toluene containing 20% trimethylamine and the solution is warmed to 70° C. The solvent is distilled off and the residue is dissolved in methanol. The solution is dehalogenated with 2.07 g of silver carbonate. The product is separated and purified by silica gel chromatography and further recrystallized from a chloroform-acetone mixture to give 2.72 g (60%) of the contemplated compound.

Elemental analysis for $C_{21}H_{45}N_2O_6P.2H_2O$: Calcd. C, 51.62; H, 10.10; N, 5.73; P, 6.34; Found C, 51.57; H, 9.88; N, 5.75; P, 6.53

IR $\nu_{max}^{KBr}$ (cm$^{-1}$): 3420, 2920, 1695, 1530, 1470, 1235, 1080.

EXAMPLE 32

3-N-Dodecylcarbamoyloxypropyl 2-trimethylammonioethyl phosphate

In 10 ml of benzene are dissolved 970 mg of the 3-hydroxypropyl carbamate obtained in Example 30 and 1.56 g of 2-(phthalimido)ethyl phosphorodichloridate, and 400 mg of pyridine is added dropwise. The mixture is stirred at room temperature and the reaction mixture is concentrated to dryness. To the residue a small amount of pyridine and water are added and the mixture is stirred at 80° C. The solvent is removed, water added, and ether extraction carried out. The extract is washed with water, concentrated to dryness and dissolved in methanol. Then, 3 ml of hydrazine hydrate is added, followed by refluxing. The solvent is distilled off, and the product is separated and purified by silica gel chromatography and recrystallized from ethanol to give 560 mg (36%) of the contemplated compound.

IR(KBr.cm$^{-1}$): 3350, 2920, 2850, 1690, 1530, 1462, 1240, 1080, 1000, 920.

Elemental analysis for $C_{18}H_{39}N_2O_6P$: Calcd. C, 52.67; H, 9.58; N, 6.82; P, 7.55; Found C, 52.59; H, 9.37; N, 6.96; P, 7.54

EXAMPLE 33

2-Methoxy-3-N-tridecylcarbamoyloxypropanol 7.99 Gram (35 mM) of tetradecanoic acid and 10.45 g (38 mM) of DPPA are treated as in Example 30, and the reaction mixture is further reacted with 44 ml of pyridine containing 11.13 g (105 mM) of β-methylglycerin to obtain 7.0 g of the contemplated alcohol. TLC [MeOH:CHCl$_3$ (1:19)] $R_f$=0.55.

NMR(60 MHz, d$_6$-DMSO): 0.7–1.6(25H), 3.01(2H), 3.35–4.3(8H), 4.70(1H), 7.10(1H).

EXAMPLE 34

2-Methoxy-3-N-tridecylcarbamoyloxypropyl 2-trimethylammonioethyl pohsphate

In 7.3 ml of benzene is dissolved 1.53 g (6.34 mM) of the alcohol obtained in Example 33, and 0.5 g of pyridine is added dropwise. The mixture is stirred vigorously at room temperature. Then, the procedure of Example 26 is followed to effect hydrolysis, quaternization with trimethylamine, dehalogenation and silica gel chromatography. The procedure provides 1.2 g of the contemplated compound as colorless powder.

IR(film)cm$^{-1}$: 3450, 2930, 2850, 1700, 1545, 1460, 1300, 1080, 1055, 960, 760.

Elemental analysis for $C_{23}H_{49}N_2O_7.0.7H_2O$: Calcd. C, 54.25; H, 9.98; N, 5.50; P, 6.08; Found C, 54.32; H, B 10.03; N, 5.93; P, 6.07

EXAMPLE 35

3-N-Tetradecylcarbamoyloxypropanol

In 200 ml of toluene is dissolved 20 g of pentadecanoic acid, followed by addition of 34 g of diphenyl phosphoroazidate and 18.7 ml of triethylamine. The mixture is stirred at room temperature for 3.5 hours. The reaction mixture is concentrated to 70 ml under reduced pressure and refluxed for 1 hour. After cooling, 23.6 g of trimethylene glycol and 124 ml of pyridine are added and the mixture is stirred at room temperature overnight. The reaction mixture is concentrated to dryness and silica gel chromatography is carried out to give 10 g of the contemplated compound.
IR$\nu_{max}^{KBr}$ (cm$^{-1}$): 1690

EXAMPLE 36

3-N-Tetradecylcarbamoyloxypropyl 2-trimethylammonioethyl phosphate

In 40 ml of benzene are added 6.3 g of the alcohol obtained in Example 35 and 7.26 g of bromoethyl phosphorodichloridate, and 2.37 g of pyridine is added dropwise under ice-cooling. The mixture is stirred at room temperature for 1 hour, the solvent distilled off, 50 ml of water added and the mixture refluxed for 1 hour. After cooling, extraction is carried out with ether and the extract is concentrated to dryness. The residue is dissolved in 50 ml of toluene solution containing 10 g of triethylamine and the mixture is warmed at 60° C. for 2 days. The solvent is replaced with methanol, dehalogenation with silver carbonate is carried out and silica gel chromatography is carried out (eluent: methanol). Recrystallization from chloroform-acetone gives 4.8 g (50%) of the contemplated compound.

Elemental analysis for $C_{23}H_{49}N_2O_6P.H_2O$: Calc. C, 55.40; H, 10.31; N, 5.62; P, 6.21; Found C, 55.10; H, 10.51; N, 5.41; P, 6.36

IR(KBr, cm$^{-1}$): 2925, 1700, 1240, 1085, 1055

EXAMPLE 37

3-N-Tetradecylcarbamoyloxypropyl 2-aminoethyl phosphate

In 40 ml of benzene are dissolved 3 g of the alcohol obtained in Example 35 and 3.8 g of 2-phthalimidoethyl phosphorodichloridate, and 1.1 g of pyridine is added dropwise. The mixture is stirred at room temperature for 3 hours and, then, concentrated to dryness. To the residue is added 16 ml of 70% aqueous pyridine solution and the mixture is stirred at 70° C. for 1.5 hours. The reaction mixture is reconcentrated to dryness, and the residue is acidified with HCl and subjected to extraction with chloroform. The solvent is replaced with methanol, 1.4 g of hydrazine hydrate added and the mixture refluxed for 30 minutes. After removal of the solvent, the product is purified by silica gel chromatography, and recrystallized from methanol to give 2.2 g (53%) of the contemplated compound.

Elemental analysis for $C_{20}H_{43}N_2O_6P.H_2O$: Calcd. C, 54.52; H, 10.08; N, 6.19; P, 7.13; Found C, 54.78; H, 9.88; N, 6.39; P, 7.06

IR(KBr cm$^{-1}$): 1690, 1520, 1413, 1213, 1080, 1010

EXAMPLE 38

3-(N-Dodecylcarbamoyloxy)-2-methoxypropanol

In 100 ml of toluene is dissolved 8.46 g of tridecanoic acid, followed by addition of 12.1 g of diphenyl phosphoroazidate and 4.44 g of triethylamine. The mixture is stirred at room temperature for 2 hours. The reaction mixture is concentrated to 60 ml and refluxed for 1 hour. After cooling, 10.6 g of glycerol β-methylether and 100 ml of pyridine are added and the mixture is stirred overnight. The solvent is distilled off, washed with water and dried. Then, silica gel chromatography [eluent: benzene-ethyl acetate (7:3)] is carried out to give 10 g of the contemplated compound.

IR $\nu_{max}^{KBr}$ (cm$^{-1}$): 1690

EXAMPLE 39

3-(N-Dodecylcarbamoyloxy)-2-methoxypropyl 2-trimethylammonioethyl phosphate

As in Example 36, a phosphate ester is produced using 6 g of the glycerol derivative of Example 38, 6.85 g of 2-bromoethyl phosphorodichloridate and 2.24 g of pyridine. Then, trimethylamination with 40 ml of toluene containing 8 g of trimethylamine and dehalogenation with silver carbonate are carried out as in Example 36, followed by silica gel chromatography to give 4.0 g of the contemplated compound.

Elemental analysis for $C_{22}H_{47}N_2O_7P.\frac{1}{2}H_2O$: Calcd. C, 53.75; H, 9.84; N, 5.70; P, 6.30; Found C, 53.58; H, 9.99; N, 5.63; P, 6.21

TLC: Rf=0.34(silica gel, CHCl$_3$—MeOH—H$_2$O, 65:25:4)

TEST EXAMPLE 1

The inhibitory effect (GD$_{50}$ values) of the compound prepared in Example 4 on the proliferation of mouse spontaneous myelolid leukemia M1 cells (resistant clone), Rauscher virus-induced promyelocytic leukemia cells R 453 and human promyelocytic leukemia cells HL-60 are 3-4 μg/ml, 2-3 μg/ml and 1 μg/ml, respectively. When determined with HL-60, the GD$_{50}$ values of the compounds prepared in Examples 25 and 26 are within the range of 2-3 μg/ml.

The following table shows GD$_{50}$ values of other compounds to human pyromyelocytic leukemia cells HL-60.

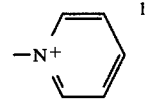

| Example No. of test compound | R$^1$ | n | R$^2$ | $-N^+\begin{smallmatrix}R^3\\-R^4\\R^5\end{smallmatrix}$ | GD$_{50}$* (μg/ (μml) |
|---|---|---|---|---|---|
| 11 | —OCONHC$_{18}$H$_{37}$ | 1 | —OCH$_3$ | —N$^+$(CH$_3$)$_3$ | 0.6 |
| 12 | —OCONHC$_{18}$H$_{37}$ | 1 | —OCH$_3$ | —N$^+$⟨ring⟩ | 1 |
| 15 | —OCONHC$_{18}$H$_{37}$ | 0 | — | —N$^+$(CH$_3$)$_3$ | 2.3 |
| 17 | —OCONHC$_{17}$H$_{29}$ | 1 | —H | —N$^+$(CH$_3$)$_3$ | 2 |
| 20 | —OCONHC$_{17}$H$_{31}$ | 1 | —H | —N$^+$(CH$_3$)$_3$ | 4.8 |
| 22 | —OCONHC$_{17}$H$_{31}$ | 1 | —H | —N$^+$H$_3$ | 4.3 |

*: HL-60 cells were cultured at various concentrations of tested compounds for a sufficient time for untreated cells to grow through four successive population doublings, and then the viable cell numbers were determined by the trypan blue dye-exclusion test. The concentrations resulting in one-half the number of control generations are listed as GD$_{50}$ values. Each value is a mean of four separate experiments.

Experimental method. (Growth inhibition, Differentiation): R. Gallo et at., Blood, Vol. 54, No. 3, 713 (1979).

TEST EXAMPLE 2

The antiprotozoal and antifungal activities of the compounds of this invention are as shown in Table 1 and Table 2.

For the antiprotozoal activity data shown in Table 1, *Tetraphymena pyriformis* W strain is used as the test microorganism and incubated at 28° C. for 44–48 hours in a test medium composed of 20 g of tryptose peptone (Difco), 1 g of yeast extract, 2 g of glucose, 1,000 ml of distilled water and 10 ml of 1 M phosphate buffer (pH 7.0), and the activity of the compounds of the invention to inhibit growth of said microorganism, in terms of MIC (minimum inhibitory concentration), is determined by the serial broth dilution technique.

For the antifungal activity data given in Table 1, *Cryptococcus neoformans* is used as the test microorganism and incubated at 37° C. for 2 days in an agar medium with a paper disc (8 mm in diameter) immersed in an aqueous 2 mg/ml solution of a test compound and air-dried as placed on said medium, and the zone of inhibition is measured. The judgement criteria are as follows: "—" means less than 9 mm in inhibition zone diameter, "±" means 9–11 mm, "+" means 12–20 mm, and "++" means more than 20 mm.

For the antifungal activity data shown in Table 2, various typical plant-disease-causing fungi are used as the test fungi and the minimum inhibitory concentration (MIC) are determined by the serial dilution technique using a 1% glucose bouillon agar medium.

TABLE 1

The antiprotozoal and antifungal activities of compounds of this invention.

| Example No. of test compound | $R^1$ | n | $R^2$ | $-N^+\begin{smallmatrix}R^3\\R^4\\R^5\end{smallmatrix}$ | MIC (μg/ml) Tetrahymena pyriformis W | Zone of inhibition Cryptococcus neuformans |
|---|---|---|---|---|---|---|
| 4 | —OCONHC$_{17}$H$_{35}$ | 1 | —H | $-\overset{+}{N}(CH_3)_3$ | 1–2 | + |
| 8 | —OCONH(CH$_2$)$_9$-  | 1 | —H | $-\overset{+}{N}(CH_3)_3$ | 40 | ... |
| 11 | —OCONHC$_{18}$H$_{37}$ | 1 | —OCH$_3$ | $-\overset{+}{N}(CH_3)_3$ | 2–4 | + |
| 12 | —OCONHC$_{18}$H$_{37}$ | 1 | —OCH$_3$ | 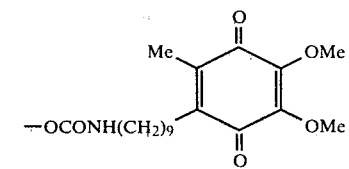 | 4 | + |
| 13 | —OCONHC$_{18}$H$_{37}$ | 1 | —OCH$_3$ | 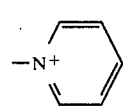 | 2–4 | + |
| 15 | —OCONHC$_{18}$H$_{37}$ | 0 | — | $-\overset{+}{N}(CH_3)_3$ | 1–2 | + |
| 17 | —OCONHC$_{17}$H$_{29}$ | 1 | —H | $-\overset{+}{N}(CH_3)_3$ | ≦1 | ++ |
| 20 | —OCONHC$_{17}$H$_{31}$ | 1 | —H | $-\overset{+}{N}(CH_3)_3$ | 2 | + |
| 21 | —OCONHC$_{17}$H$_{31}$ | 0 | — | $-\overset{+}{N}(CH_3)_3$ | 2 | ± |
| 22 | —OCONHC$_{17}$H$_{31}$ | 1 | H | $-\overset{+}{N}H_3$ | ≦1 | ± |
| 18 | —OCONHC$_{17}$H$_{29}$ | 1 | H | $-\overset{+}{N}H_3$ | 2–4 | + |
| 25 | —OCONHC$_{14}$H$_{29}$ | 1 | —OCH$_3$ | $-\overset{+}{N}H_3$ | =1 | ++ |
| 26 | " | 1 | " | $-\overset{+}{N}(CH_3)_3$ | 0.2 | + |
| 28 | —OCONHC$_{10}$H$_{21}$ | 1 | " | $-\overset{+}{N}H_3$ | 2 | — |
| 29 | —OCONHC$_{10}$H$_{21}$ | 1 | —OCH$_3$ | $-\overset{+}{N}(CH_3)_3$ | 2 | ± |
| 23 | —OCONHC$_{13}$H$_{17}$ | 1 | H | $-\overset{+}{N}(CH_3)_3$ | ≦0.1 | + |
| 31 | —OCONHC$_{12}$H$_{25}$ | 1 | H | $-\overset{+}{N}(CH_3)_3$ | ≦1 | + |
| 32 | " | 1 | H | $-\overset{+}{N}H_3$ | ≦1 | + |
| 36 | —OCONHC$_{14}$H$_{29}$ | 1 | H | $-\overset{+}{N}(CH_3)_3$ | ≦1 | ++ |

TABLE 2

The antifungal activity of the compounds synthesized in Examples [MIC (μg/ml)]

| Fungi | Example No. of test compound | | | | | | |
|---|---|---|---|---|---|---|---|
| | 4 | 17 | 25 | 26 | 23 | 31 | 36 |
| Pyricularia oryzae | 6.25 | 25 | 6.25 | 3.12 | 6.25 | 12.5 | 3.12 |
| Cochliobolus miyabeanus | >100 | 25 | >100 | 12.5 | 12.5 | 12.5 | 25 |
| Gibberella fujikuroi | >100 | 50 | 50 | 12.5 | 25 | 50 | 12.5 |
| Botrytis cinerea | 12.5 | 12.5 | 6.25 | 3.12 | 6.25 | 12.5 | 12.5 |
| Leptosphaeria salvinii | 50 | 50 | 100 | 6.25 | 12.5 | 25 | 6.25 |
| Colletotrichum lagenarium | 50 | 25 | 100 | 6.25 | 6.25 | 3.12 | 6.25 |
| Aspergillus | >100 | 50 | 25 | 12.5 | 12.5 | 12.5 | 12.5 |
| Penicillium | >100 | 50 | 25 | 12.5 | 12.5 | 12.5 | 12.5 |
| Red yeast | >100 | 100 | 50 | 25 | 12.5 | 25 | 25 |
| Brewer's yeast | >100 | 100 | 25 | 6.25 | 12.5 | 12.5 | 6.25 |

PREPARATION EXAMPLE 1

Injection

In 1.0 liter of distilled water is dissolved 80 g of 3-(N-tetradecylcarbamoyloxy)-2-methoxypropyl 2-trimethylammonioethyl phosphate, and the solution is subjected to sterile filteration. With one milliliter each of the solution are filled 1000 vials under sterile conditions, and then lyophilized, followed by sealing the vials. On the other hand, two liters of injectable solution containing 100 g of xylitol or mannitol is prepared, and with 2 ml of the solution are filled 1000 ampoules for injection, and thus filled ampoules are sealed under sterile conditions.

They are used as injection by dissolving the powder of one vial in the injectable xylitol or mannitol solution.

PREPARATION EXAMPLE 2

Tablet

| (1) | 3-(N—Octadecylcarbamoyloxy)-2-methoxypropyl 2-pyridinioethyl phosphate | 100 mg |
|---|---|---|
| (2) | Lactose | 200 mg |
| (3) | Corn-starch | 51 mg |
| (4) | Hydroxypropyl cellulose | 9 mg |

The above ingredients per tablet are mixed and granulated by a conventional manner. To the granules are added corn-starch (8 mg) nd magnesium stearate (2 mg), and the mixture is compressed by a tabletting machine to prepare a tablet of 9.5 mm diameter, weighing 370 mg.

What is claimed is:

1. A compound of the formula:

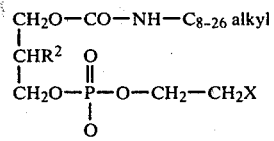

wherein $R^2$ is H or methoxy and X is pyridinio or thiazolio or a pharmaceutically acceptable salt thereof.

2. A compound according to claim 1 wherein X is pyridinio.

3. A compound according to claim 2 wherein the $C_{8-26}$-alkyl group is octadecyl.

4. A compound according to claim 1 wherein X is thiazolio.

5. A compound according to claim 4 wherein the $C_{8-26}$ alkyl group is octadecyl.

* * * * *